(12) United States Patent
Cinti

(10) Patent No.: US 8,574,172 B2
(45) Date of Patent: Nov. 5, 2013

(54) APPARATUS AND PROCESS FOR MONITORING A PREGNANT MAMMAL

(76) Inventor: Enrico Cinti, Piacenza (IT)

( * ) Notice: Subject to any disclaimer, the term of this patent is extended or adjusted under 35 U.S.C. 154(b) by 254 days.

(21) Appl. No.: 13/128,557

(22) PCT Filed: Nov. 9, 2009

(86) PCT No.: PCT/EP2009/064837
§ 371 (c)(1),
(2), (4) Date: May 10, 2011

(87) PCT Pub. No.: WO2010/055011
PCT Pub. Date: May 20, 2010

(65) Prior Publication Data
US 2011/0224581 A1   Sep. 15, 2011

(30) Foreign Application Priority Data

Nov. 11, 2008 (IT) .............................. PN2008A0085

(51) Int. Cl.
*A61B 5/117* (2006.01)
*A61B 5/103* (2006.01)

(52) U.S. Cl.
USPC .......................................... 600/588; 600/591

(58) Field of Classification Search
USPC ........... 600/588, 591; 606/119; 235/376, 492; 340/539.1, 539.12, 573.3
See application file for complete search history.

(56) References Cited

U.S. PATENT DOCUMENTS

| 4,232,686 | A | | 11/1980 | Kammlade, Jr. | |
| 6,039,701 | A | * | 3/2000 | Sliwa et al. | 600/588 |
| 2002/0010390 | A1 | | 1/2002 | Guice et al. | |
| 2008/0128486 | A1 | * | 6/2008 | Lowe | 235/376 |
| 2009/0012432 | A1 | * | 1/2009 | Sharf | 600/588 |

FOREIGN PATENT DOCUMENTS

| FR | 2 582 933 | 12/1986 |
| WO | 2008 117834 | 10/2008 |

OTHER PUBLICATIONS

International Search Report issued Jan. 27, 2010 in PCT/EP09/64837 filed Nov. 9, 2009.

* cited by examiner

*Primary Examiner* — Brian Szmal
(74) *Attorney, Agent, or Firm* — Oblon, Spivak, McClelland, Maier & Neustadt, L.L.P.

(57) ABSTRACT

Apparatus for monitoring a pregnant mammal including: a sensor (11) operatively associated with a mammal to detect a condition of delivery of said mammal; a transmission circuit (15), operatively associated with said sensor (11), to generate and transmit a notification signal (100) based on the detection of said sensor (11), and a processing unit (20) operatively associated with said sensor (11) to receive said notification signal (100) and generate a corresponding communication signal (110) for an operator. The description also covers a process for monitoring a pregnant mammal.

11 Claims, 1 Drawing Sheet

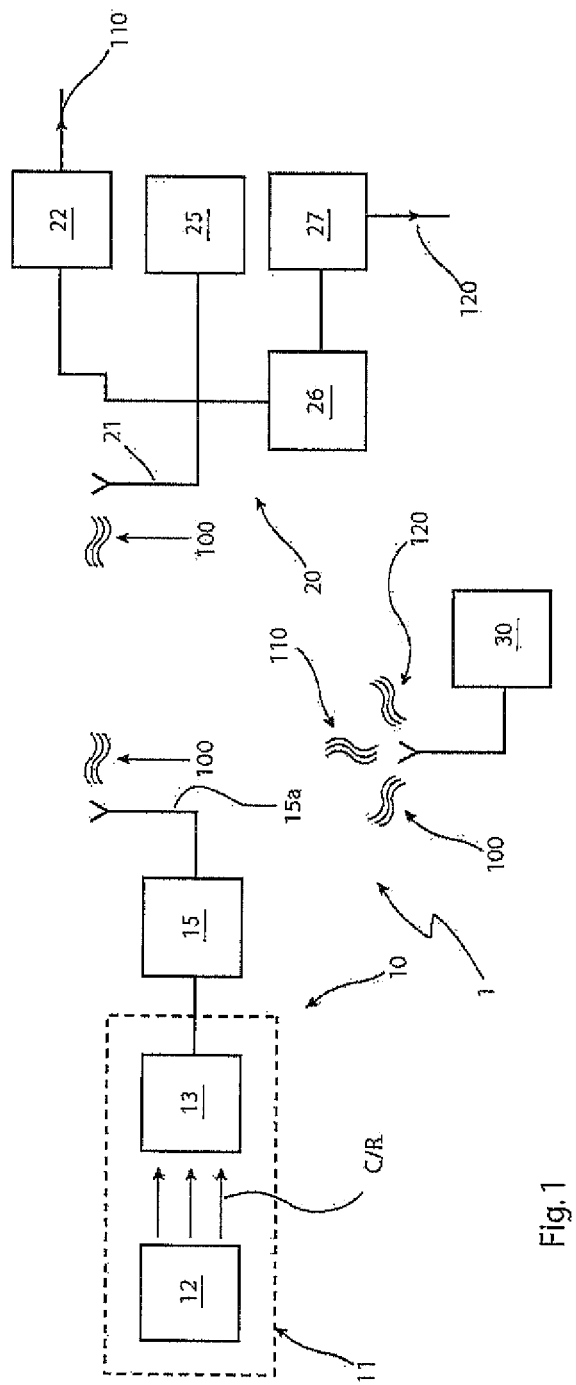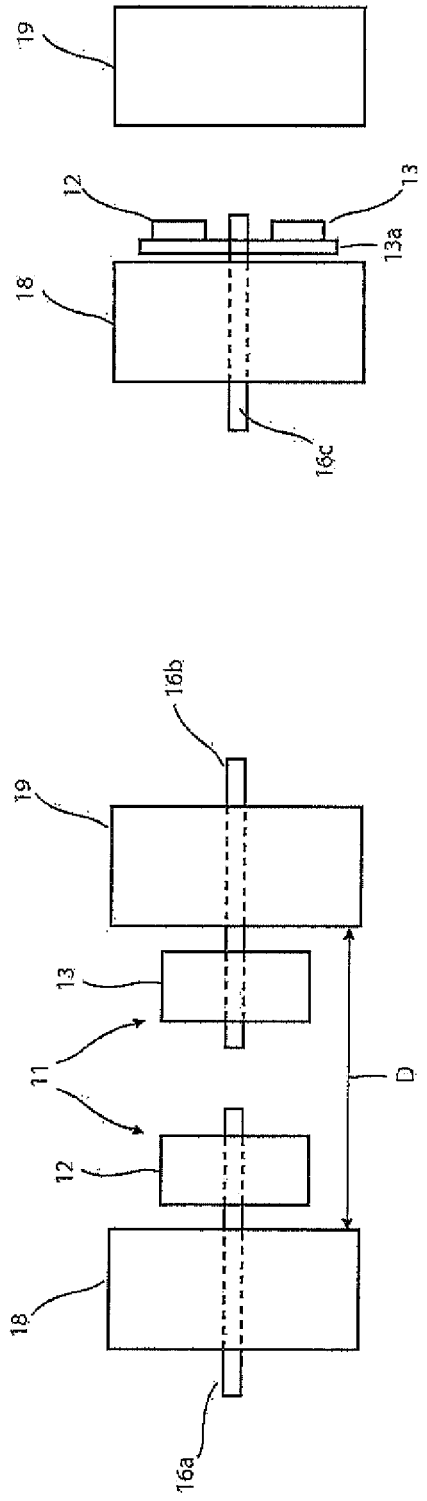

APPARATUS AND PROCESS FOR MONITORING A PREGNANT MAMMAL

TECHNICAL FIELD OF INVENTION

The present invention relates to an apparatus and a process for monitoring a pregnant mammal.

TECHNICAL BASIS OF INVENTION

As is well known, during the life of a mammal the delivery is a crucial phase, in which both the animal giving birth and the animal being born are exposed to a variety of risks that could involve complications and relative consequences on the health of both animals.

For example, in the case of pig breeding, there is still a very high death rate occurring in the birthing phase (stillborn piglets).

Moreover, in view of continuous genetic improvements and the consequent tendency of increases in the number of offspring delivered at the end of each pregnancy, there is a correspondingly high risk that the number of stillborn piglets will also increase.

The main causes of this problem may be the following:
- for what concerns piglets: fetal hypoxia (due to the displacement of the piglet along the birth canal and to the consequent constriction of the umbilical cord); excessively low weight (which implies that the piglet is less vital, has a smaller oxygen reserve and is too weak to withstand the stress of parturition);
- for what concerns the parturient sow: genetic; influence; size of litter; parturition number; duration of parturition; number of stillborn in previous deliveries; physical condition; stress (due for example to ambient temperature, to the behaviour of the operators tending the animal, etc.); diseases, such as for example hypocalcaemia, anaemia, other conditions (Aujeszky's disease, various enteroviruses, eperythrozoonosis, erysipelas, leptospirosis, parvovirus, PRRS [Porcine Reproductive and Respiratory Syndrome], toxoplasmosis, mycotoxycosis;
- for what concerns human factors: mistaken interpretation of events during parturition; inappropriate supervision of the birthing event; human behaviours or excessive supervision (which increase the mother's stress); incorrect induction (inappropriate use of prostaglandin and oxytocin); vaginal palpation.

Therefore, there is a need, perceived particularly in breeding farms, to monitor pregnant animals, particularly in the phase nearing the delivery, so as to face in a prompt and appropriate manner any type of situation that may arise.

At present, the whole process is assigned to the attention of the operators who personally supervise the sows, waiting for the delivery to take place and making sure that the birthing of the piglets is non accompanied by any complication.

There are evident shortcomings in this context in terms of waste of time and energy, due the fact that it is not possible to foretell in a sufficiently reliable manner the moment when the birth will take place, and it is therefore required that one or more operators stand near the expectant sow, paying attention to the imminent birthing of the piglets.

This necessarily entails significant losses of time, without considering that the operator may inevitably be subject to moments of decreased attention, especially in the case of particularly long waits as at night-time, so that the monitoring activity could be unreliable or even useless.

The only alternative at present is hormonal induction, which provides for the use of prostaglandin, possibly combined with oxytocin, and which makes it possible to induce labour and to determine its start fairly accurately.

However, this technique also has its own drawbacks, because the moment when the hormones are administered must be chosen in an extremely accurate manner (and is therefore extremely difficult to determine exactly), in order to have a successful induction, and so as not to further increase the risk of having various stillborn piglets.

It is therefore evident that the hormonal induction of delivery cannot be considered an acceptable solution of the problems as exemplified above.

One attempt to resolve the above drawbacks has been described in the French patent application FR 2 582 933, which discloses a remote automatic device that signals the start of a birth including an electromagnetic sensor applied to a vulvar labium of a female animal and a conventional sensor applied to the other labium, a radiofrequency transmitter connected by cables to said sensors capable of transmitting signals to a receiver. However, such device makes it possible to detect only the start of the delivery, since the sensors are such as to detect the start of the parting of the vulvar labia, which is an early sign of the expulsion. Consequently, it does not make it possible to have a continuous monitoring during the entire delivery phase, and therefore to detect if problems could arise after the first phase.

U.S. Pat. No. 4,232,686 discloses a start-of-delivery remote detection apparatus provided with a radio transmitter, a power supply suitable to be attached to the female animal, and a breakable signal transmission assembly applied with adhesives astride the vaginal orifice of the animal. Even in this case, the apparatus can only detect the start of the delivery, that is the parting of the vaginal labia before the expulsion, since once the assembly is broken it is no longer possible to monitor additional situations such as, for example, a second delivery in pluriparous animals or the non-complete expulsion of the animal being delivered.

SUMMARY OF THE INVENTION

The objective of the present invention is therefore to provide an apparatus and a process for monitoring a pregnant mammal making it possible to provide the operator with data and/or signals useful to objectively and reliably assess the risk having stillborn offspring in the delivery phase.

Another objective of the present invention is to provide an apparatus and a process capable of also operating in a manner at least partially independent of the operators, thus without requiring their continuous supervision.

An auxiliary objective of the present invention is to provide an apparatus and a process that also make it possible to signal any possible complications that may occur during the mammalian delivery.

These and other objectives are substantially achieved by the equipment and process described in the attached claims.

BRIEF DESCRIPTION OF FIGURES

Additional characteristics and advantages will become more evident from the detailed description of a preferred but not exclusive embodiment of the invention.

This description is provided with reference to the attached figures, having themselves a purely illustrative and therefore not limiting purpose, in which:

FIG. 1 illustrates a block diagram of the apparatus in accordance with the invention;

FIG. 2 illustrates a block diagram of a device forming a part of the apparatus of FIG. 1;

FIG. 3 illustrates an embodiment of the device of FIG. 2.

DETAILED DESCRIPTION OF THE INVENTION

With reference to the attached figures, reference numeral 1 generally indicates an apparatus for monitoring a pregnant mammal according to the present invention.

The apparatus 1 is applicable in the breeding field, in particular in the breeding of pigs, cattle, buffaloes and similar animals; obviously, the apparatus 1 can also be employed on any other species of mammals, preferably breeding mammals.

The apparatus 1 includes first of all a device 10 (FIGS. 1-3), predisposed for monitoring a pregnant mammal.

The device 10 is attached to a respective pregnant mammal, so as to be able to determine, as will become more evident hereinbelow, the moment of the expulsion of one or more offspring being delivered.

The device 10 includes in fact a sensor 11 to detect a condition of parturition of the mammal.

This condition of parturition can be determined, for example, by the passage of an offspring through the vaginal opening of the mammal.

In addition or as an alternative, the condition of parturition can be determined by a reciprocal parting, beyond a preset threshold, of the mammal's vaginal labia. The preset threshold can be, for example, a rest threshold (for example, 2 cm), beyond which there is a change of state of the measurement that begins to be at a very high frequency (for example, 10 measurements a second). Moreover, the measurement can preferably be one of distance/time and not only distance, as will be better explained hereinbelow, so as to also reduce the "false positive" signals.

Preferably, the sensor 11 can be associated with one or more of the mammal's vaginal labia 18, 19 to detect the abovementioned delivery condition.

The device 10 also includes a transmission circuit 15, operatively connected to the sensor 11, to generate and transmit a notification signal 100 based on the detection of the same sensor 11.

In particular, as will become more evident hereinbelow, the notification signal 100 is generated when the sensor 11 detects a parturition condition in the mammal being monitored.

The sensor 11 can detect a passage, through the mammal's vaginal opening, of an offspring being delivered.

In addition or as an alternative, the sensor 11 can detect a reciprocal parting of the vaginal labia 18, 19 of the mammal beyond a preset threshold.

Based on the condition of the mammal being monitored, the sensor 11 can be piloted from a first to a second operating condition.

In the first operating condition, the sensor 11 does not detect a condition of parturition of the mammal, and therefore it does not enable power to be supplied to the transmission circuit 15; therefore, the notification signal 100 is not generated or transmitted.

In the second operating condition, the sensor 11 detects a parturition condition of the monitored mammal, and therefore allows power supply to the transmission circuit 15, so that the notification signal 100 can be generated and transmitted.

In light of the above, it is clear that the sensor 11 is in the first operating condition when no offspring to be delivered is going through the vaginal opening of the mammal, and/or when the vaginal labia 18, 19 of the same mammal are not parted beyond the preset threshold.

On the other hand, the sensor 11 is in the second operating condition when at least one offspring is passing through the vaginal opening of the mammal, and/or when the vaginal labia 18, 19 of the same mammal are parted beyond the preset threshold.

It should be noted that, due to the physical and functional connection between the sensor 11 and the transmission circuit 15, the latter can be prearranged to generate a notification signal 100 for each animal being delivered (that is, independently of whether the sensor 11 detects the passage of each offspring through the vaginal opening of the mammal or detects the parting of the vaginal labia 18, 19).

Furthermore, the notification signal generated can advantageously be a continuous and variable or modulated signal. In other words, the signal emitted by the sensor and sent to a suitable processing unit, as will be better explained hereinbelow, is not of the On-Off type but it is a continuous signal that reaches said unit during a preset time span with variable characteristics that depend on the course of the phase of delivery, starting from the parting of the vaginal labia beyond a value indicating a normal condition, going through the whole course of said parting and the expulsion of the offspring and continuing unto the vaginal labia return to a condition, as the case may be, that is normal or preparatory for a subsequent delivery.

As an alternative, said notification signal may be generate and sent at longer or shorter time intervals and with variable characteristics that are indicative of the condition of delivery, as previously explained.

Preferably, the sensor 11 includes a generating element 12 that generates an electromagnetic field C and/or a radiation R, and a detecting element 13 that is sensitive to said electromagnetic field C and/or to said radiation R.

It should be noted that, in the present context and in the subsequent claims, the expression "electromagnetic field" is taken to include static magnetic fields, static electrical fields, electromagnetic fields in which both the electric field vector and the magnetic field vector are not constant in time.

The expression "radiation" includes any emission capable of propagating in the air, such as for example optical, acoustic and electromagnetic radiation.

In particular, the radiation R is a radiation that is not capable of propagating through the body of the animals being delivered, or that however propagates through such bodies in a significantly lesser degree than it propagates through the air.

Preferably, the generating element 12 is associable to a first vaginal labium 18 on the mammal, while the detecting element 13 is associable to a second vaginal labium 19 of the same mammal (FIG. 2).

More particularly, the generating element 12 and the detecting element 13 are mounted on the respective labia 18, 19 by means of a "piercing" technique.

This means that, in the preferred embodiment, in each vaginal labium 18, 19 is inserted a thin stem 16a, 16b, preferably having a cylindrical shape with a diameter between 1 mm and 2 mm; to each end of the stem is fastened a respective closing head (non shown), so that the same stem cannot be drawn out of the labium in which it is inserted.

Each of the elements 12, 13 is thus preferably engaged in the corresponding vaginal labium 18, 19 through a respective stem 16a, 16b.

In particular, it has been found that the use of the "piercing" technique makes it possible to obtain an optimum fastening of the elements 12 and 13. In fact, in accordance with conventional techniques, the use of dermocompatible glues such as those with a cyanoacrylate base are subject to crystallization and lose their elastic and adhesive properties when they are in contact with moisture in general, and in particular with urine and fetal liquids. The result is that said elements detach rapidly, and thus nullify monitoring. Similarly, it has been found that the use of clips cannot guarantee a sure fastening of the elements either, due to the relaxation of the tissues. In fact, the cups are applied to the mucous membrane of the vaginal labia which, after the relaxation caused by the natural conditions of the animal due to the effect of the delivery preparatory hormones and/or to the effect of rubbings caused by the animal itself due to the discomfort and itch caused by the cups, detach very easily.

Conversely, the "piercing" system was tested and was found to represent the most advantageous system both for the function of attachment and for the very limited discomfort caused to the animal.

Preferably, the generating element 12 and the detecting element 13 are attached to the respective labia 18, 19 so as to face each other, as shown schematically in FIG. 2.

In particular, the elements 12, 13 are mounted in contact with the internal surfaces of the respective labia 18, 19, that is, with the surfaces of the labia 18, 19 on either side of the vaginal opening of the mammal.

In the embodiment in which the generating element 12 and the receiver element 13 are mounted on respective labia 18, 19, the sensor 11 can detect the passage of the offspring through the vaginal opening of the monitored mammal, and/or the parting of the labia 18, 19.

In the first case, the offspring to be delivered, immediately before being expelled is at least partially interposed between the generating element 12 and the detecting element 13, and prevents the latter from detecting the electromagnetic field C and/or the radiation R.

In this situation, the sensor 11 moves to the same operating condition and enables the generation of the notification signal 100.

In the second case, it should be noted that the moment in which the offspring is ready to be expelled, the vaginal labia 18, 19 of the parent animal undergo a reciprocal parting to allow the offspring to come out completely.

When such parting exceeds a preset threshold, which can be defined as a value, for example, between 5 and 20 cm, and in particular between 7 and 9 cm in the case of a piglet, the receiving element 13 is no longer capable to detect the field C and/or the radiation R generated by the generating element 12, and the sensor 11 switches to the second operating condition.

On the other hand, when the delivery is not yet imminent, the distance D between the labia 18, 19 is typically less than 2 cm (and in effect substantially nil), and the sensor 11 remains in the first operating condition.

As an alternative, the sensing element 11 and the receiving element 13 can work in continuous conditions as previously explained.

As an alternative, both the generating element 12 and the receiving element 13 can be attached to the same vaginal labium 18, 19 (FIG. 3).

In particular, the generating element 12 and the receiving element 13 can be mounted on the same vaginal labium 18, 19, preferably through a "piercing" technique that is in all effects similar to the one described above.

In greater detail, the generating element 12 and the detecting element 13 are fastened to an internal surface of a same vaginal labium 18, 19, that is, to the surface of the labium 18, 19 facing the vaginal opening of the mammal, so as to be able to monitor what is happening around that opening. A further advantage over gluing comes from the fact that the internal application limits the possibility of the sensors becoming detached as a result of accidental rubbing or of the animal lying down.

The generating element 12 and the receiving element 13 can be fastened separately to the vaginal labium 18, 19, or they can be engaged on the same support 13a, and thus connected to the vaginal labium 18, 19 through a single connecting element, provided for example by a stem 16c.

In this configuration, when the offspring passes through the vaginal opening of the monitored mammal, the field C and/or the radiation R emitted by the generating element 12 are reflected at least in part by the body of the offspring, and can therefore be sensed by the detecting element 13; consequently, the sensor 11 switches to the second operating condition to allow the generation of the notification signal 100.

On the other hand, when there are no imminent deliveries and the emission from the generating element 12 is not reflected, the sensing element 13 does not detect substantially anything and the sensor 11 remains in the first operating condition.

It should be noted that in FIG. 3 the generating element 12 and the sensing element 13 are mounted on the same first labium 18, it is evident that they can both be mounted, in an entirely similar way, on the second labium 19.

Preferably, the generating element 12 can include a plurality of portions, oriented in ways that are different from each other, in this manner, it is possible to obtain different directions of generation of the electromagnetic field C, so as to still allow a correct and reliable interaction between the generating element 12 and the detecting element 13.

Preferably, the detecting element 13 can include a plurality of portions, oriented in ways that are different from each other. In this manner, it is possible to obtain different directions of detection of the electromagnetic field C, so as to still allow a correct and reliable interaction between the generating element 12 and the detecting element 13.

If should in fact be noted that, due to the movements of the animal that is about to give birth (or that is actually delivering) and due to the natural relaxation of the vulvar tissues, the reciprocal positioning of the generating element 12 and of the detecting element 13 is not always fixed; thanks to the technical device described above, it is thus also possible to deal with this last problem.

In particular, in the case in which the generating element 12 is prearranged for the generation of a magnetic field (as in the various examples given hereunder), the generating element is designed to include at least two permanent magnets, oriented perpendicularly with respect to each other.

The sensor 11 can be a Hall sensor; in this case, the generating element 12 is a magnet or a similar element suitable for generating a magnetic field, while the detecting element 13 can be a plate of metallic or semiconductive material, with a predetermined current made to flow through it by applying a certain voltage to its ends. As long as the sensor 11 is in the first operating condition, the plate is immersed in the magnetic field generated by the element 12, and the electrical charges within it are consequently distributed in a direction perpendicular to the direction of flow of said current. The moment in which the sensor 11 is in the second operating condition, the influence of the field generated by the element 12 on the plate is negligible, and the distribution of the charge within it becomes substantially uniform (at least in the direction perpendicular to the direction of flow of the current). The measuring range of a Hall sensor reaches 4-5 cm.

The two different types of charge distribution are thus used to selectively activate the supply to the transmission circuit 15.

The sensor 11 can be a magnetoresistive sensor. In this case, the generating element 12 generates a magnetic field, while the detecting element 13 has an electric resistance that varies on the basis of the magnetic field in which the detecting element 13 is immersed. Hence, when the sensor 11 is in the first operating condition, the detecting element 13 and the circuitry connected to it will be sized so that no power is supplied to the transmission circuit 15, whereas when the sensor 11 is in the second operating condition, the resistance) of the detecting element 13 will be such that the transmission circuit 15 will be suitably supplied and the notification signal 100 will be generated. The measuring range, unlike the abovementioned Hall sensor, reaches up to 10-13 cm. In this range, the measurement is continuous.

The sensor 11 can be a Reed sensor. In this case, the generating element 12 generates a magnetic field, while the detecting element 13 includes a pair of thin sheets near each other and preferably substantially parallel. When the two sheets are immersed in the field generated by the generating element 12 (first operating condition), they remain in contact with each other by virtue of the magnetic attraction that develops between the sheets and that overcomes their resistance to deformation. When the sensor 11 is in the second operating condition, the sheets spread apart from each other and, as a result of this circuital condition, power is supplied to the transmission circuit 15.

It is evident that the types of sensors specified above have been indicated merely by way of example; depending on requirements, other types of sensors can be used, providing they are capable to carry out the detection function described above.

For example, generators and detectors of optical, acoustic, electromagnetic, electromechanical and other radiation can be used, provided they can correctly distinguish the condition of delivery of the mammal being monitored.

Preferably, the sensors used are of magnetoresistive type. It should be remembered, in fact, that a magnetoresistive sensor relies on the GMR (Giant Magneto Resistor) technology, considerably more sensitive than the Hall sensors or the Reed sensors, like those adopted by the known art indicated in the introductory part of the present description. For example, such sensors make it possible to measure variations in the electromagnetic field on three Cartesian axes so as to perfectly monitor the movements of the vulvar labia and, therefore, to discriminate with precision any positive false signals, that is, pre-delivery as against the actual delivery, or to detect and adapt to the sensor-magnet misalignment due to the natural relaxation of the tissues. In addition, it is possible to vary the characteristic of the signal that the sensor sends to the processing unit, as previously explained and with all the advantages already indicated.

More preferably, the magnetoresistive sensors are position or proximity sensors capable of detecting the distance between two points, in this case between the generating element 12 and the detecting element 13, each positioned on a vulvar labium. The detection takes place continually; in other words, the position sensors constantly send a signal whose characteristic varies based on the distance between the labia. Alternatively, the detection comes about at regular intervals so as to cover the entire time span from the start of the parting of the labia to their subsequent closing after the expulsion.

In the case in which the generating element 12 includes a plurality of generating portions or single generating devices (as for example a plurality of magnets), it is advantageously arranged that the generating element itself 12 be provided with a housing, in which said portions or devices are suitably positioned.

Preferably, the transmission circuit 15 is provided with an antenna 15a, so that the notification signal 100 can be transmitted by radio-frequency technology.

It should be noted that, in one embodiment, the notification signal 100 can be sent directly to an operator, who is in turn provided with a radio-frequency device 30 to receive the same notification signal 100.

In addition or as an alternative, the notification signal 100 can be sent to a processing unit, which will be better described below.

The apparatus 1 may in fact include a processing unit 20 operatively connected to the device 10 to receive at least the notification signal 100, preferably through an antenna 21, and to generate a corresponding communication signal 110 for an operator.

In this manner, it is possible for example to limit the hardware/software requirements of the device, which can be pre-arranged to communicate only with the processing unit 20. This unit will in turn contact one or more operators, that is, the radio-frequency devices 30 with which said operators are provided, in accordance with suitable procedures, so that the delivery can be kept under control.

To generate the communication signal 110 based on the notification signal 100, the processing unit 20 can be provided with an operating module 22.

Advantageously, the processing unit 20 may include a counting block 25 to count the number of offspring delivered by the mammal to which the device 10 is connected.

This information can then be stored, for example, for management purposes connected with the organization of the whole breeding farm.

Preferably, the counting block 25 carries out its task on the basis of the notification signals 100 received; in fact, as mentioned above, the device 10 is preferably predisposed to generate a notification signal 100 for each offspring that is expelled by the parturient mammal.

Moreover, in the preferred embodiment, the processing unit 20 includes a time measurement block 26 to measure time intervals between subsequent notification signals 100 in pluriparous animals.

This means that the time measurement block 26 carries out a measurement of the time that elapses between the expulsion of one offspring and the expulsion of the next one; in this manner, it is possible to supply data to the operator, who can then analyze them and promptly detect the occurrence of problems or complications.

In fact, for what concerns for example swine, up to 12-14 piglets can be expelled on the average in every delivery, and the interval from one expulsion to the next is on the average 20-30 minutes; in the case of an excessively long wait between one expulsion and the next, it may be that complications occurred, which could be recognized almost immediately and would allow an operator to take prompt action.

For this purpose, the processing unit 20 can be provided with an alarm module 27, operatively associated with the time measurement block 26 to generate an alarm signal 120, should an interval between two deliveries turn out to be longer than a predefined threshold.

In light of the above, it is clear that the apparatus 1 may include a plurality of devices 10, each mounted on a respective mammal waiting to give birth, so that the various animals may be suitably monitored.

Each device 10 can be prearranged to transmit its own notification signal 100 to the processing unit 20, which then handles the different information received.

In particular, the processing unit 20 may include a computer such as a personal computer, an interface monitor and antennas for radio-frequency connection with the abovementioned sensors. The computer will be provided with a software suitable to run on appropriate hardware of commercial type. The hardware will be capable of receiving the signals sent by said sensors and of converting them into data that will be processed by the software.

Advantageously, the processing of said data by the software includes the comparison with data stored in a memory unit present in said hardware in order to verify any coincidence or lack of coincidence and the degree of deviation from said stored data indicative of a state of normalcy of the parturient animal, a pre-delivery state, a start of delivery, various states of progress of the birthing process, and a state of completion of delivery. If the detected signals result in data which deviate from predefined memorized reference values, the software will be capable of piloting the system to issue an alarm signal visible through the abovementioned interface and/or an audible signal for the operator.

Preferably, as previously explained, the aforesaid data representative of the state of the parturient animal include data indicative of the distance or parting of the vaginal labia starting from a value that identifies the normal situation in which the labia are substantially still in contact with each other and proceeding then to values that represent a sequence of measurements of increasing distances, up to a value that, compared with the reference memorized values, is indicative of the expulsion of the offspring being delivered. Moreover, the software will also compare the date processed by the signals with those memorized for what regards the post-expulsion phase in order to verify that the animal returns to normal conditions and, as the case may be, if it is preparing correctly and without complications for the next delivery. This last processing will take place, then, by recording and comparing measurements of said distance between the labia in a decreasing rather than an increasing tendency.

More preferably, the software will be capable of also processing, concurrently with said positioning or distance signals, the notification signals detected by said counting and time measurement blocks to also control and compare with the stored data the number, and therefore to perform a count, and the time intervals of the duration of one delivery and/or the duration between one delivery and the next. The comparison with stored reference data, as before, makes it possible to have an even finer control of the overall situation of the animal and of the offspring being delivered so as to provide the operator with a picture of the situation as complete as possible and remotely available, to avoid stressing the animal and, as mentioned, allow prompt action in case of problems. In fact, even in this case, if the data detected deviate by predefined values from the normal memorized reference data, the software will cause the hardware to issue the aforesaid alarm signal, which could be of different nature, such as for example visual and/or acoustic, and/or an electronic message.

To enable a correct identification of the individual devices 10, and thus of the animals from which the notification signals 100 originate, each device 10 can be associated with a univocal identifying code, which tells it apart from the other devices 10.

The notification signal 100 preferably contains the identifying code of the device 10 that generated it, so as to enable the processing unit 20 to recognize the origin of the notification signal itself 100, and allow a proper management of the information even in the case in which various animals deliver during at least partially overlapping time intervals.

The processing unit 20 may then be provided with a suitable chart, in which the various data relative to the devices 10 and to the animals associated with them are available.

Preferably, the processing unit 20 is not located in the same place where the devices 10 are installed, that is, inside the structure in which the animals are normally kept.

The processing unit 20 can thus be advantageously positioned several tens of metres away, in a place protected from dirt, dust, etc., which are considerably present where the animals are herded.

In this context, a particular advantage is the abovementioned radio-frequency connectivity between the devices 10 and the processing unit 20 which allows the transmission of the notification signal 100 without the necessity of cabled connections.

It should be noted that the various functional blocks described above with reference to the processing unit 20 are not necessarily realized as hardware modules physically distinct from each other; in effect, such blocks may be formed through a single computer, such as for example a conventional PC or a similar computer, suitably programmed to perform the various functions indicated.

The invention achieves important advantages:

First of all, the apparatus and the process according to the invention are extremely precise and reliable.

In addition, the apparatus and the process forming the subject matter of the present invention can also operate correctly in a manner at least partially independent of the attendant operators, therefore without requiring a continuous supervision from the same operators.

Another advantage lies in the fact that the apparatus and the process according to the invention are also capable of providing indications on any complications that may occur in the course of the delivery process of the mammal.

The invention claimed is:

1. A system for monitoring a pregnant breeding animal, comprising:
   a detecting device configured to detect a change of state, including
      a magnetoresisitive position sensor that measures variations in an electromagnetic field on three Cartesian axes to detect a condition of a delivery of offspring of the breeding animal, the sensor including
         a generating element configured to generate an electromagnetic field, and
         a detecting element that is sensitive to the electromagnetic field, each of the generating element and the detecting element being adapted to be secured to one of a single labium and different labia of the breeding animal, and
      a transmission circuit, operatively associated with the sensor, the transmission circuit configured to generate and transmit a notification signal based on a detection of the condition of the delivery;
   a processing unit, operatively associated with the detecting device the processing unit configured to receive the notification signal and to generate a corresponding communication signal for an operator, and the processing unit including a counter configured to count a number of the offspring which have been delivered by the breeding animal during the delivery,
   wherein the detecting device is configured to generate and transmit the notification signal at least one of continuously and at preset intervals throughout the delivery to continually indicate the condition of the delivery, the notification signal being relative to detection of at least one of passage of the offspring through a vaginal opening of the breeding animal and parting of vaginal labia of the breeding animal beyond a preset threshold, and wherein the notification signal is configured to indicate different states of at least one of the passage and the parting.

2. The system according to claim 1, wherein the processing unit further comprises a time measuring device including a timer to measure time intervals between the notification signal and a subsequent notification signal, and an alarm module operatively associated with the timer to generate an alarm signal when an interval between the notification signal and the subsequent notification is equal to or exceeds a predefined threshold.

3. The system according to claim 1, wherein the sensor comprises:

a mechanism for attaching the sensor to the vaginal labia of the breeding animal using a piercing.

4. The system according to claim 1, wherein, when one of a condition in which no offspring is going through the vaginal opening of the breeding animal and a condition in which the vaginal labia of the breeding animal is not parted beyond the preset threshold, the sensor functions in a first operating condition in which power does not flow to the transmission circuit, and wherein, when one of the condition in which offspring is going through the vaginal opening of the breeding animal and the condition in which the vaginal labia of the breeding animal is parted beyond the preset threshold, a second operating condition in which power is supplied to the transmission circuit and there is a consequent generation of the notification signal.

5. A method for monitoring a pregnant breeding animal, comprising:

securing a magnetoresisitive position sensor to the breeding animal, the sensor measuring variations in an electromagnetic field on three Cartesian axes, the sensor including a generating element configured to generate an electromagnetic field, and a detecting element that is sensitive to the electromagnetic field, and the securing the sensor to the breeding animal including securing each of the generating element and the detecting element to one of a single labium and different labia of the breeding animal, sensing a state of a delivery of the breeding animal using the sensor;

generating and transmitting a notification signal, based on an output of the sensor;

receiving and processing the notification signal;

comparing the notification signal with stored information;

generating a communication signal indicating the state of the delivery using a result of the comparing; and counting, via a processing unit including a counter configured to count, a number of offspring delivered by the breeding animal during the delivery;

wherein the generating of the communication signal occurs at least at one of continually and at preset intervals during one of a passage of the offspring through a vaginal opening of the breeding animal and parting of vaginal labia of the breeding animal beyond a preset threshold to indicate different states of the delivery.

6. The method according to claim 5, wherein the generating and transmitting comprises:

enabling the generating and transmitting of the notification signal, when the sensing detects the passage of the offspring through the vaginal opening of the breeding animal; and not enabling the generating and transmitting of the notification signal, when the sensing does not detect the passage of the offspring through the vaginal opening of the breeding animal.

7. The method according to claim 5, wherein the generating and transmitting comprises:

enabling the generating and transmitting of the notification signal, when the sensing detects the parting of the vaginal labia beyond a preset threshold; and not enabling the generating and transmitting of the notification signal, when the sensing does not detect the parting of the vaginal labia beyond the preset threshold.

8. The method according to claim 5, wherein the communication signal indicates a distance or positioning of the parting of the vaginal labia due to a position of the offspring, from a value indicating a normal position, in which the vaginal labia are in contact with each other, to values which indicate distances of separation between the vaginal labia.

9. The method according to claim 5, further comprising measuring a duration of the delivery.

10. The method according to claim 9, further comprising comparing the duration which has been measured with reference data.

11. The method according to claim 10, further comprising generating an alarm signal when the duration deviates from a predefined reference value, in response to the comparing the duration.

* * * * *